United States Patent
Borsook et al.

(10) Patent No.: US 7,860,552 B2
(45) Date of Patent: Dec. 28, 2010

(54) CNS ASSAY FOR PREDICTION OF THERAPEUTIC EFFICACY FOR NEUROPATHIC PAIN AND OTHER FUNCTIONAL ILLNESSES

(75) Inventors: David Borsook, Concord, MA (US); Lino Becerra, Cambridge, MA (US); Marnie Shaw, Millswood (AU)

(73) Assignee: The McLean Hospital Corporation, Belmont, MA (US)

( * ) Notice: Subject to any disclaimer, the term of this patent is extended or adjusted under 35 U.S.C. 154(b) by 619 days.

(21) Appl. No.: 11/240,007

(22) Filed: Sep. 30, 2005

(65) Prior Publication Data
US 2006/0074298 A1 Apr. 6, 2006

Related U.S. Application Data

(60) Provisional application No. 60/615,239, filed on Oct. 1, 2004.

(51) Int. Cl.
*A61B 5/05* (2006.01)

(52) U.S. Cl. .................. 600/410; 600/407; 600/322; 600/340; 600/473; 600/476; 514/46; 514/49; 514/564

(58) Field of Classification Search ............ 600/410, 600/322, 340, 504, 407, 544, 473, 476, 411, 600/431; 514/46, 49, 564
See application file for complete search history.

(56) References Cited

U.S. PATENT DOCUMENTS

| 5,905,069 | A | 5/1999 | Borsook et al. |
|---|---|---|---|
| 6,066,163 | A | 5/2000 | John |
| 6,907,280 | B2 | 6/2005 | Becerra et al. |
| 7,196,071 | B2 | 3/2007 | Borsook |
| 7,375,094 | B2 | 5/2008 | Borsook |
| 2002/0019364 | A1* | 2/2002 | Renshaw ............ 514/46 |
| 2002/0042563 | A1 | 4/2002 | Becerra et al. |
| 2002/0058867 | A1 | 5/2002 | Breiter et al. |
| 2003/0211459 | A1 | 11/2003 | Breiter et al. |
| 2004/0038927 | A1 | 2/2004 | Borsook |
| 2004/0096089 | A1 | 5/2004 | Borsook et al. |
| 2006/0078183 | A1 | 4/2006 | deCharms |
| 2006/0253014 | A1 | 11/2006 | Borsook et al. |
| 2007/0161597 | A1 | 7/2007 | Borsook |
| 2008/0039737 | A1 | 2/2008 | Breiter et al. |
| 2008/0207557 | A1 | 8/2008 | Borsook |

OTHER PUBLICATIONS

International Search Report for International Patent Application No. PCT/US2005/035050, mailed Dec. 6, 2006.
Borsook et al., "CNS Response to a Thermal Stressor in Human Volunteers and Rats May Predict the Clinical Utility of Analgesics," *Drug Discovery Research* 68: 23-41 (2007).

* cited by examiner

*Primary Examiner*—Brian Casler
*Assistant Examiner*—John F Ramirez
(74) *Attorney, Agent, or Firm*—Clark & Elbing LLP

(57) ABSTRACT

In general, the invention features methods for identifying therapeutic interventions for functional illnesses, e.g., neuropathic pain or depression, and methods for identifying markers for functional illnesses by employing an acute painful stimulus or other stimulus for a functional illness and measuring levels of CNS activity.

13 Claims, 8 Drawing Sheets

A

B

CNS ASSAY FOR PREDICTION OF THERAPEUTIC EFFICACY FOR NEUROPATHIC PAIN AND OTHER FUNCTIONAL ILLNESSES

CROSS-REFERENCE TO RELATED APPLICATIONS

This application claims benefit of U.S. Provisional Application No. 60/615,239, filed Oct. 1, 2004, which is hereby incorporated by reference.

BACKGROUND OF THE INVENTION

In general, the invention relates to the field of functional illnesses.

Many functional illnesses, e.g., pain and psychiatric disorders, may be correlated with central nervous system (CNS) activity. These illnesses are, however, typically assayed based on interviews or psychological tests. In addition, symptoms of a functional illness may be confused with an unrelated illness, or an unrelated illness may mask an underlying functional illness. Because of these limitations, functional illnesses are difficult to diagnose definitively, and the effectiveness of treatments may also be difficult to discern. This difficulty is exacerbated when a subject is unwilling or unable to articulate symptoms.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus. Extensive electrophysiological research in animals has defined likely neuroanatomical substrates for some of the sensory attributes of pain, such as localization and intensity, and some of the adaptive responses, such as descending analgesia. Other regions activated by painful stimuli have also been identified which may be involved in the affective response; however, the neural substrates for the motivational and emotional response to pain remain a topic of debate.

In general, pain conditions can be divided into chronic and acute. Chronic pain includes neuropathic pain (e.g., post surgical and postherpetic neuralgia) and chronic inflammatory pain (e.g., arthritis), or pain of unknown origin (e.g. fibromyalgia) while acute pain usually follows non-neural tissue injury (e.g., tissue damage from surgery or inflammation, or migraine). Non-invasive techniques that measure neuronal activity in humans, including magnetoencephalography (MEG), single proton emission tomography (SPECT), positron emission tomography (PET) and functional magnetic resonance imaging (fMRI), are now being used to discern CNS pathways involved in pain.

Testing pharmacological agents in humans usually requires a number of steps including testing in healthy subjects and in patients with the disease, thus requiring the exposure of a large number of human subjects to a drug. In addition, quantitative data on drug screening in humans may also be difficult to obtain, especially for functional illnesses.

SUMMARY OF THE INVENTION

In general, the invention features methods for identifying therapeutic interventions for functional illnesses and methods for identifying markers for functional illnesses by employing an acute painful stimulus or other stimulus for a functional illness and measuring levels of CNS activity.

In one aspect, the invention features a method for identifying a therapeutic intervention for a functional illness including the steps of administering a candidate therapeutic intervention to a subject; administering an acute painful stimulus to the subject; and measuring the level of activation of the central nervous system (CNS) indicative of the functional illness in the subject, wherein a modification of the level of CNS activation relative to a control level of activation characteristic of the functional illness is indicative of the efficacy of the candidate therapeutic intervention for the functional illness.

The subject may or may not be suffering from the functional illness. The control may be an image of the CNS of a control subject, wherein the therapeutic intervention had not been administered to the control subject.

The invention also features a method for identifying a marker for a functional illness, including the steps of administering a stimulus for the functional illness to a subject, wherein the subject is not suffering from the functional illness; measuring the level of activation of the CNS in the subject; and comparing the levels of CNS activation to a control level of CNS activation to identify the marker for the functional illness. The stimulus is, for example, an acute painful stimulus or an visual, auditory, olfactory, tactile, or gustatory stimulus. The control may be an image of the CNS of a control subject, wherein the stimulus has not been administered to the control subject.

The invention also features a method for identifying a therapeutic intervention for a psychiatric disorder including the steps of administering a candidate therapeutic intervention to a subject; administering a stimulus for the psychiatric disorder to the subject; and measuring the level of activation of the CNS in the subject, wherein a modification of the level of CNS activation relative to a control level of CNS activation characteristic of the psychiatric disorder is indicative of the efficacy of the candidate therapeutic intervention for the psychiatric disorder. The subject may or may not be suffering from the psychiatric disorder. The control may be an image of the CNS of a control subject, wherein the therapeutic intervention has not been administered to the control subject.

In various embodiments of the invention, the subject is a mammal, such as a human or rat. The functional illness may include chronic pain or a psychiatric disorder. An exemplary chronic pain condition is neuropathic pain, which may include post herpetic neuralgia, HIV neuropathy, diabetic neuropathy, Fabry's disease, peripheral neuropathy, trigeminal neuralgia, post incisional neuropathic pain, phantom limb pain, reflex sympathetic dystrophy, causalgia, anesthesia dolorosa, intercoastal neuralgia, post-traumatic localized pain, complex regional pain syndrome, or neuropathic pain caused by trauma, lead, or chemotherapy. Exemplary psychiatric disorders include an affective disorder, an anxiety disorder, attention deficit hyperactivity disorder, a memory disorder, post traumatic stress disorder, a psychotic disorder, a substance abuse disorder, an addiction, a phobia, or obsessive compulsive disorder, as described herein. The therapeutic intervention may include a compound, a physical stimulus, an electrical stimulus, a thermal stimulus, electromagnetic radiation, counseling, or a surgical, medical, or dental procedure, or a combination thereof. The therapeutic intervention may also be administered subtherapeutically. Examples of acute painful stimuli include a change in temperature, mechanical force, a pin prick, or administration of a compound. The level of activation is measured, for example, by a neuroimaging device, such as a functional magnetic resonance device, positron emission tomography (PET) device, a magnetoencephalography (MEG) device, an electroencephalography (EEG) device, a single photon emission computer tomography (SPECT) device, an infrared (IR) device, a diffuse optical tomography (DOT) device, a magnetic resonance spectroscopy (MRS) device, or a functional computerized tomography (CT) device. When a control is used, the same individual, or animal, may both be assayed by the methods described herein and serve as the control. The level of activation may be measured in one or more regions of the CNS, e.g., the orbital gyrus (Gob), ventral tegmentum/periaqueductal gray VT/PAG, nucleus accumbens (NAc), sublenticular extended amygdala (SLEA), cingulate gyrus, primary somatosensory cortex (S24), secondary somatosensory cortex (S2), thalamus, insula, cerebellum, prefrontal cortex, amygdala, hypothalamus, parahippocampal gyrus, hippocampus, entorrhinal cortex, ventral pallidum, dorsal striatum, primary motor cortices (M24), secondary motor cortices (M2), supplementary motor cortex (SMA), frontal eye field (FEF), rostral ventralmedial medulla (RVM), cerebellum, lateral prefrontal cortex, middle frontal gyri (Brodmann areas 44, 45, 46, 47), superior frontal gyri (Brodmann areas 6, 8), or brainstem subnuclei. Alternatively, the level of activation is not measured with reference to specific regions of the CNS.

By "acute pain" is meant pain of short duration that resolves completely and follows direct stimuli such as trauma (e.g., resulting from acute injury or surgery), inflammation, or burns. Typically, acute pain ceases when the stimulus is removed or the injured tissue has healed.

By "acute painful stimulus" is meant a stimulus that evokes acute pain in a subject.

By "chronic pain" is meant persistent pain that is not caused by an acute stimulus. Most commonly, chronic pain results from a pathological condition such as infection, arthritis, chronic injury (e.g., sprain), cancer, migraine, irritable bowel disease, visceral pain disorders (e.g., chronic pancreatitis), and neuropathic pain. Chronic pain may also be idiopathic, e.g., fibromyalgia. Such pain may persist long after the inciting event.

By "functional illness" is meant chronic pain or a psychiatric disorder.

By "marker for a functional illness" is meant a characteristic level of activation in the CNS that is indicative of the functional illness. The marker may include a pattern of activation of specific regions or a measure of the general level of activation in the CNS, or portion thereof.

By "neuropathic pain" is meant pain caused by peripheral nerve or central nervous system damage (e.g., stroke or spinal cord trauma). Neuropathic pain may include, without limitation, a burning sensation, hyperpathia, dysaethesia, allodynia, or phantom pain. Exemplary types of neuropathic pain include infective (e.g., post herpetic neuralgia and HIV neuropathy), metabolic (e.g., diabetic neuropathy and Fabry's disease), toxic (e.g., from lead or chemotherapy), traumatic/stretch injury (e.g., post incisional, trauma, phantom limb pain, and reflex sympathetic dystrophy/complex regional pain syndrome/causalgia), and idiopathic (e.g., trigeminal neuralgia/tic douloureux).

By "psychiatric disorder" is meant a condition that affects mood or behavior. Exemplary psychiatric disorders include affective disorders (such as depression, bipolar disorder, mania, and dysphoria), anxiety disorders (such as anxiety and panic disorder), attention deficit hyperactivity disorder, memory disorders, post traumatic stress disorder, psychotic disorders (such as schizophrenia and schizoaffective disorder), substance abuse disorders, addictions, phobias, and obsessive compulsive disorder.

By "therapeutic intervention" is meant a regimen intended to have a preventive, ameliorative, curative, or stabilizing effect. Examples of therapeutic interventions include pharmaceutical compositions, physical stimuli (e.g., massage or acupuncture), electrical stimuli, thermal stimuli, electromagnetic radiation, counseling, or a surgical, medical, or dental procedure.

Other features and advantages will be apparent from the following description and the claims.

DETAILED DESCRIPTION OF THE INVENTION

Surprisingly, we have found that the use of a stimulus that evokes acute pain in a subject can be used to assay functional illnesses, e.g., chronic pain, which are often refractory to traditional assay treatment methods. That is, the acute painful stimulus may be used to probe illnesses that are unrelated in pathology to acute pain. Based on this finding, the invention features methods for identifying therapeutic interventions useful for the treatment of a functional illness and methods for identifying a marker for a functional illness.

Figure 1:
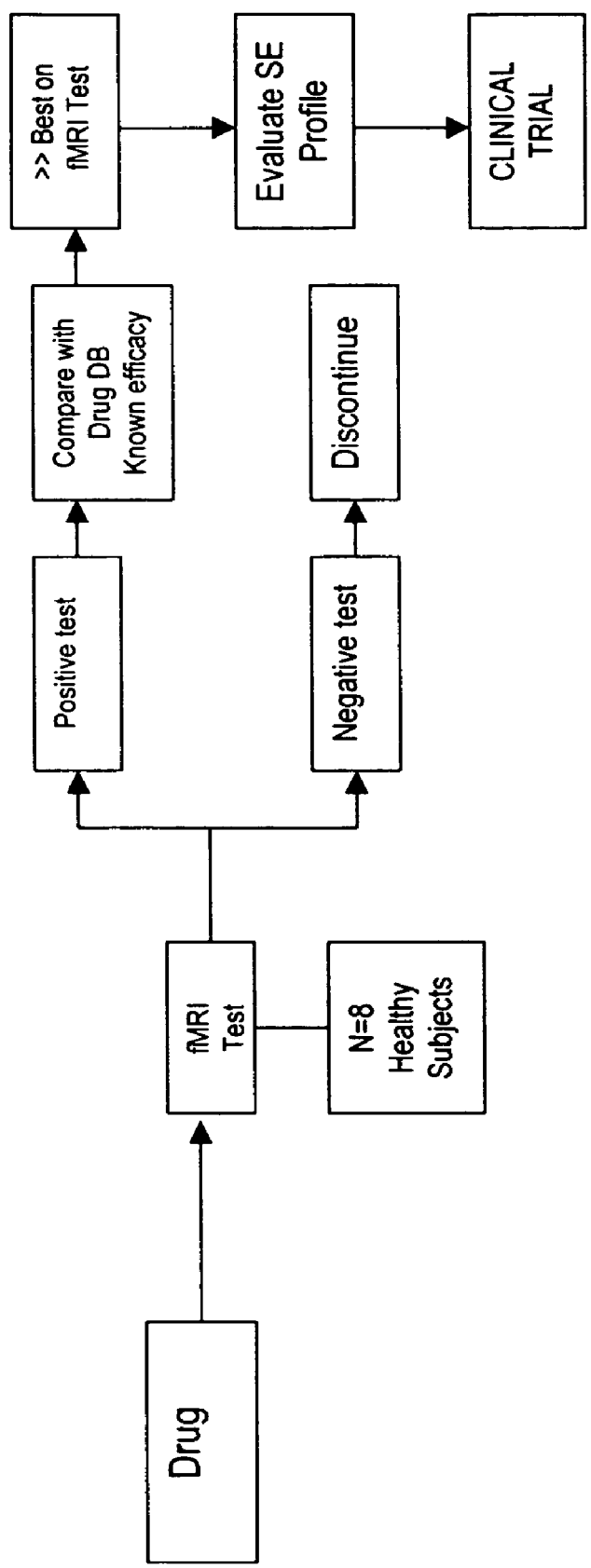
FIG. 1 is a flowchart of a method of the invention as applied to neuropathic pain. The method is general for functional illnesses.

The methods of the invention generally involve the administration of a therapeutic intervention, e.g., a compound, to a subject, e.g., a mammal such as a human, non-human primate, or a rodent (e.g., a rat or mouse). In one embodiment, an acute painful stimulus, e.g., a thermal stimulus, is then administered to the subject. An appropriate time delay may be used in order to achieve appropriate therapeutic effect in the blood and/or CNS prior to administration of the stimulus. Levels of activation of the central nervous system (CNS) of the subject are then measured, typically by a neuroimaging technique such as fMRI. When a therapeutic intervention is being evaluated for efficacy against the functional illness, the levels of activity are examined to determine whether the intervention alters activity in the CNS (FIG. 1). The levels of activity may be determined with reference to one or more specific regions of the CNS, such as those associated, either directly or indirectly with the functional illness, or a general level of activity for the entire CNS, or portion thereof, may be determined without reference to specific anatomical or functional regions. Any alteration in the level of activity may be determined relative to a control, such as levels of activity in a subject treated with placebo or a therapeutic intervention with known efficacy against the functional illness. The method is advantageous in that the subject need not be suffering from the functional illness in order to determine the efficacy of a therapeutic intervention for the illness. Alternatively, the subject may be suffering from the illness, and the stimulus is employed to activate the CNS, e.g., in one or more regions associated with the illness, either directly or indirectly. An exemplary acute painful stimulus is a thermal stimulus, e.g., a probe that is heated above 44° C. Additional stimuli include those that provide mechanical force, pricking or cutting, electrical shock, and chemical agents. Other acute painful stimuli are known in the art.

In an alternative embodiment, the method employs a stimulus that activates the CNS in a way that is indicative of a psychiatric disease, which may or may not be in common with chronic pain. Appropriate stimuli for various psychiatric disorders are known in the art and include stimuli for all senses, e.g., visual, auditory, olfactory, tactile, and gustatory. For example, for studying anxiety, photos or other visual cues that induce anxiety may be employed as stimuli. In another example, visual, auditory, or other sensory stimuli that mimic the presenting condition that may have caused post traumatic stress disorder (e.g., war, motor vehicle accident, abuse, or torture) are employed. Furthermore, gain/loss games may be used as stimuli for gambling addiction. As above, the method is advantageous in that the method may employ healthy subjects, i.e., those not suffering from the psychiatric disorder, in order to evaluate therapeutic interventions.

To identify a marker for a functional illness, a stimulus for the functional illness, as discussed herein, is administered to a subject not suffering from the illness. The levels of activation of the CNS of the subject are then measured and compared to a control to identify the marker. The control may include, for example, levels of activation from a healthy subject not subjected to the stimulus.

Any intervention may be employed in the methods described herein, for example, pharmaceuticals, such as organic compounds, inorganic compounds, peptides or proteins, and nucleic acids (e.g., gene products). Additional interventions include physical stimulation (e.g., via massage or acupuncture), thermal stimulation (warm or cold), electromagnetic radiation, electrical stimulation, counseling, or a surgical, medical, or dental procedure, or a combination thereof. In methods of the invention, therapeutic interventions may be administered at subtherapeutic levels. A therapeutic intervention may also be administered once or for a short duration. In addition, a small number of subjects may be employed (e.g., 6-10). Methods of determining efficacy of an intervention may also be used to determine the length of time that a particular intervention is effective by periodically monitoring activation as a function of time. Methods of determining efficacy may also be used to quantify the effects of a particular intervention, e.g., to determine proper dosing or frequency and possible synergistic or detrimental interactions with other interventions.

The methods of the invention may be used for any functional illness in which an appropriate stimulus activates or deactivates the CNS, e.g., in one or more regions that are associated with the functional illness. Exemplary functional illnesses include chronic pain, e.g., neuropathic pain, and psychiatric disorders, e.g., depression, phobias, and anxiety.

Imaging Techniques

The present invention typically employs an imaging technique for measuring the level of activation of the CNS, e.g., by determining blood flow in the CNS. Such techniques to monitor the CNS, or specific portions thereof, allow for the determination of the presence, intensity, duration, and type of CNS activity experienced by a subject, e.g., activated, deactivated, or unchanged regions of the CNS. Typically, the level of activation is identified by observation of a localized increased blood flow to an area of the CNS. Exemplary regions of the CNS that may be monitored include the orbital gyrus (Gob), ventral tegmentum/periaqueductal gray VT/PAG, nucleus accumbens (NAc), sublenticular extended amygdala (SLEA), cingulate gyrus, primary somatosensory cortex (S24), secondary somatosensory cortex (S2), thalamus, insula, cerebellum, prefrontal cortex, amygdala, hypothalamus, parahippocampal gyrus, hippocampus, entorrhinal cortex, ventral pallidum, dorsal striatum, primary motor cortices (M24), secondary motor cortices (M2), supplementary motor cortex (SMA), frontal eye field (FEF), rostral ventralmedial medulla (RVM), cerebellum, lateral prefrontal cortex, middle frontal gyri (Brodmann areas 44, 45,46, 47), superior frontal gyri (Brodmann areas 6,8), and brainstem subnuclei. These regions may provide a direct measure of a particular CNS activity or may be indirectly related to such activity. In addition, the imaging methods may also be employed to determine a general level of activation for the CNS, e.g., measured as the total number of activated voxels., without regard to the specific regions involved.

The level of activation of the CNS may be determined from an imaging technique using any method known in the art. For example, measurements from the CNS of a subject may be compared to various standards in order to determine a level of activation, e.g., as indicated by the localized blood flow. Standards include a reference measurement from the subject when not suffering from the functional illness, a reference measurement from an inactivated portion of the CNS, or a reference from another subject, or aggregate of subjects, not experiencing the functional illness (e.g., a standard control image). The regions of one or both hemispheres may be monitored, and the region in one hemisphere may serve as a reference for the other.

The actual region of the CNS detected may vary depending on the particular use. In addition, an initial image of a subject may be obtained to identify the location of a particular region in the CNS. Once identified, a smaller area encompassing all or a portion of the particular region may be monitored. For example, the location of highest intensity may be monitored as a function of time.

Imaging techniques that may be used in the methods of the invention include a functional magnetic resonance device (fMRI), a positron emission tomography (PET) device, a magnetoencephalography (MEG) device, an electroencephalography (EEG) device, a single photon emission computer tomography (SPECT) device, an infrared (IR) device, a diffuse optical tomography (DOT) device, a magnetic resonance spectroscopy (MRS) device, and a functional computerized tomography (CT) device.

EXAMPLE 1

Evaluation of a Therapeutic Compound

Figure 2:
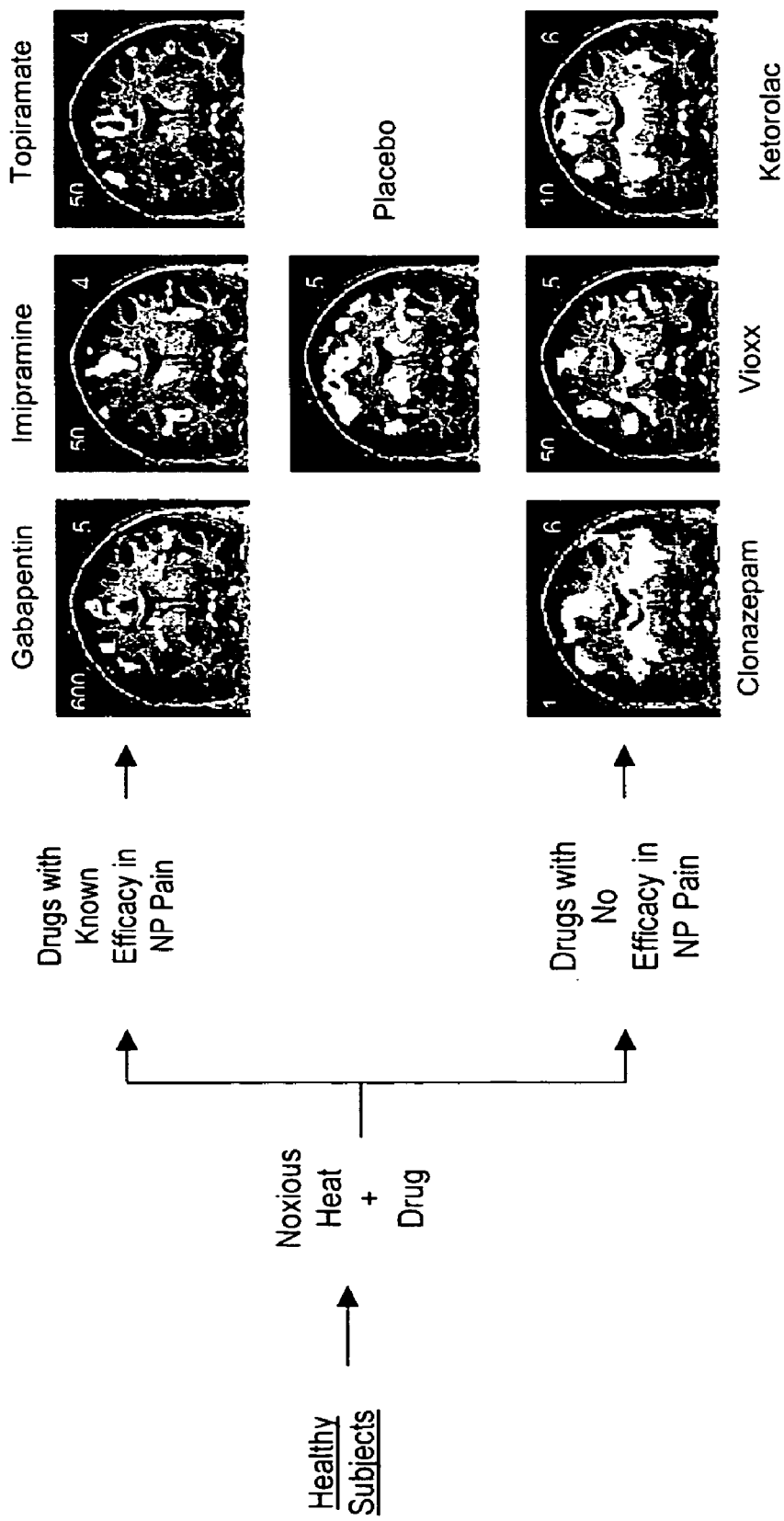
FIG. 2 is a series of fMRI data on the effect of three drugs with known therapeutic efficacy in neuropathic pain (NP)—gabapentin, imipramine, and topiramate—all showing a decreasing signal change following the heat stimulus—and three drugs with no efficacy in neuropathic pain—all showing no effect. Typical drug dosing (mg/70 kg) used is indicated in the top left hand corner of each fMRI image. The number needed to treat (NNT), indicated in the top right hand corner, is the number of subjects given the therapy for the first subject to have a 50% decrease in pain. The NNT for effective drugs is typically less than that for placebo and for drugs that are not effective for neuropathic pain.

A series of therapeutic compounds were administered to healthy subjects, who were subjected to a thermal stimulus (>44° C.) after the therapeutic compound had been administered. The results are shown in FIG. 2. The top row of fMRI images indicates that drugs with known efficacy for neuropathic pain showed significant effect on CNS activation after the stimulus (i.e., overall decrease in fMRI activation). In contrast, the bottom row of images indicates that compounds that are not effective for neuropathic pain show no effect (i.e., no change in fMRI activation) or increased effect (i.e., increase in fMRI activation) compared with the placebo response (middle image).

Figure 3:
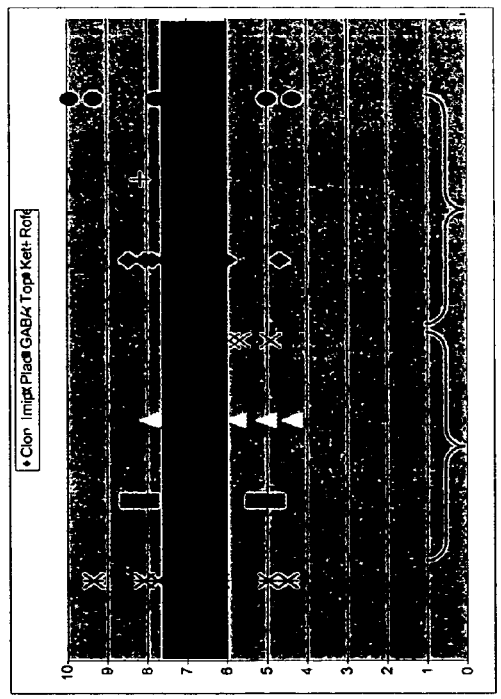
FIGS. 3A-3B are graphs of results of a visual analog scale (VAS) and the method of the invention. (A) Subjective rating of pain (VAS 0-10 where 0 is no pain and 10 is the maximum pain imaginable) does not show any difference between therapeutic compounds following noxious heat (the drugs are administered at relatively low doses). (B) The total number of activated voxels (positive and negative) measured by fMRI quantitatively differentiate between the two groups—drugs with efficacy in neuropathic pain (gabapentin, imipramine, and topiramate) vs. drugs with no efficacy (clonazepam, rofecoxib, and ketorolac).
Figure 3:
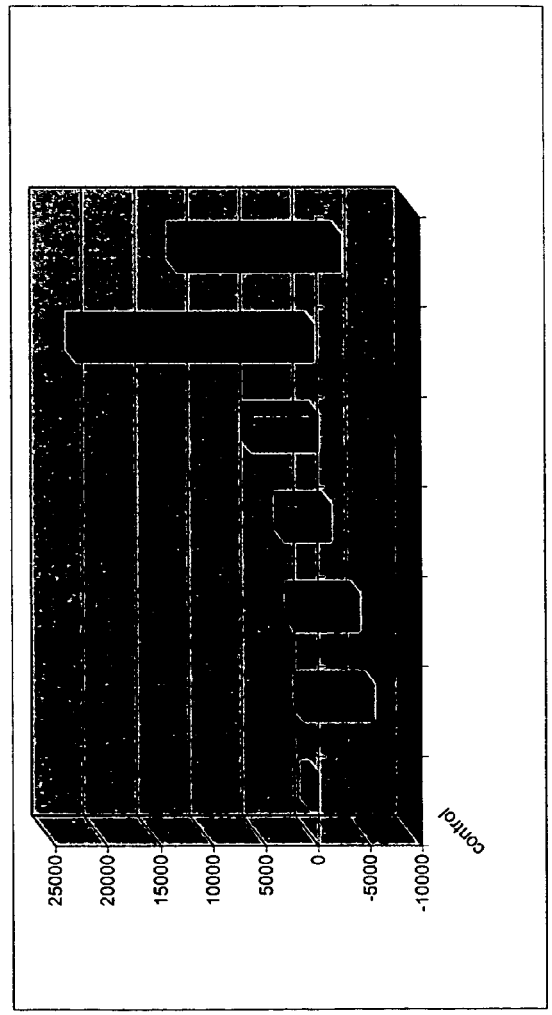

FIGS. 3A and 3B show how the methods of the invention provided quantitative analysis of therapeutic compounds as opposed to subjective reporting by the subject. There was no difference between the subjective report for compounds that are effective for neuropathic pain and for compounds that are not effective for neuropathic pain. In contrast, quantitative data (as measured by the total number of activated voxels in fMRI images shown in FIG. 2) showing differences between the groups of effective and non-effective compounds were obtained using the methods described herein.

EXAMPLE 2

Use of Rats as a Model for Efficacy in Humans

Figure 4:
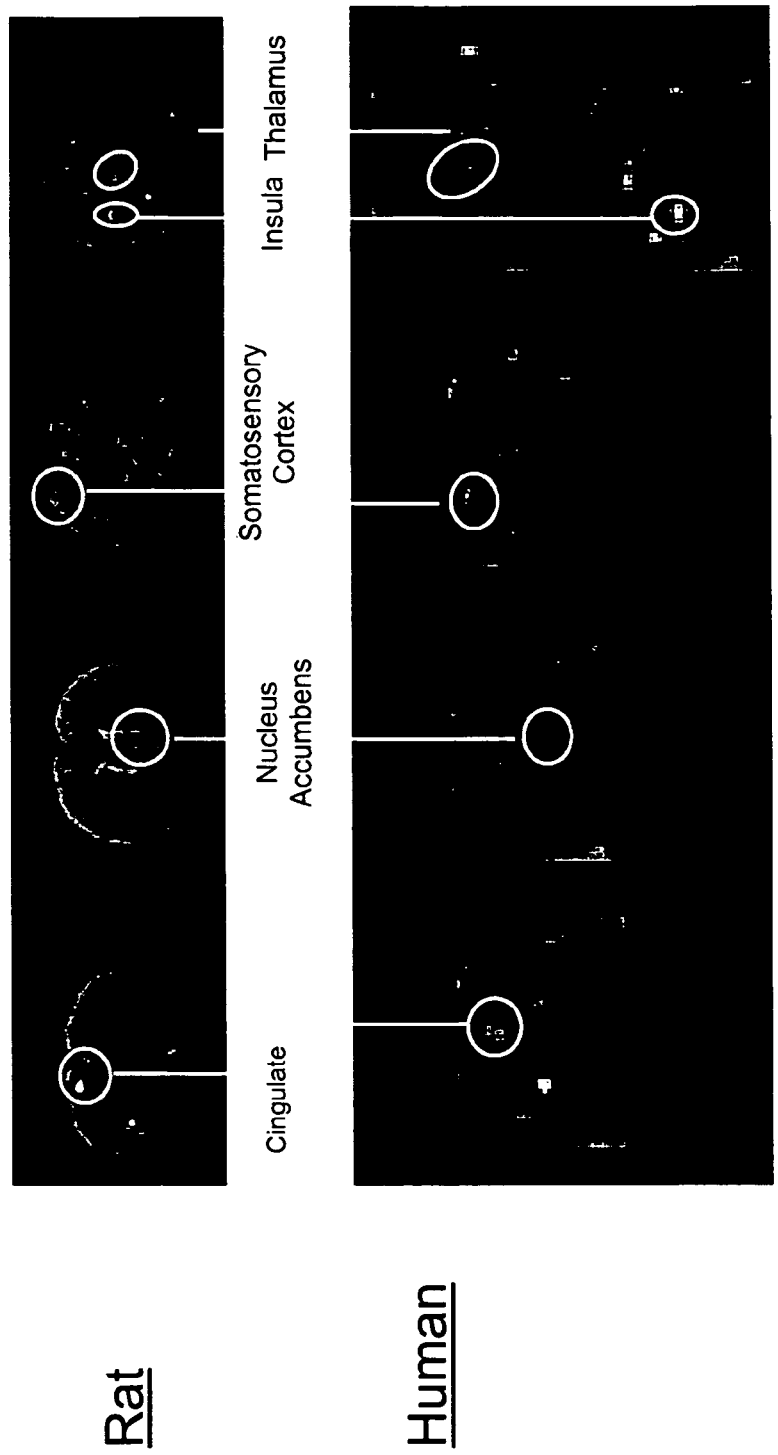
FIG. 4 is a series of fMRI images comparing human and rat subjects.
Figure 5:
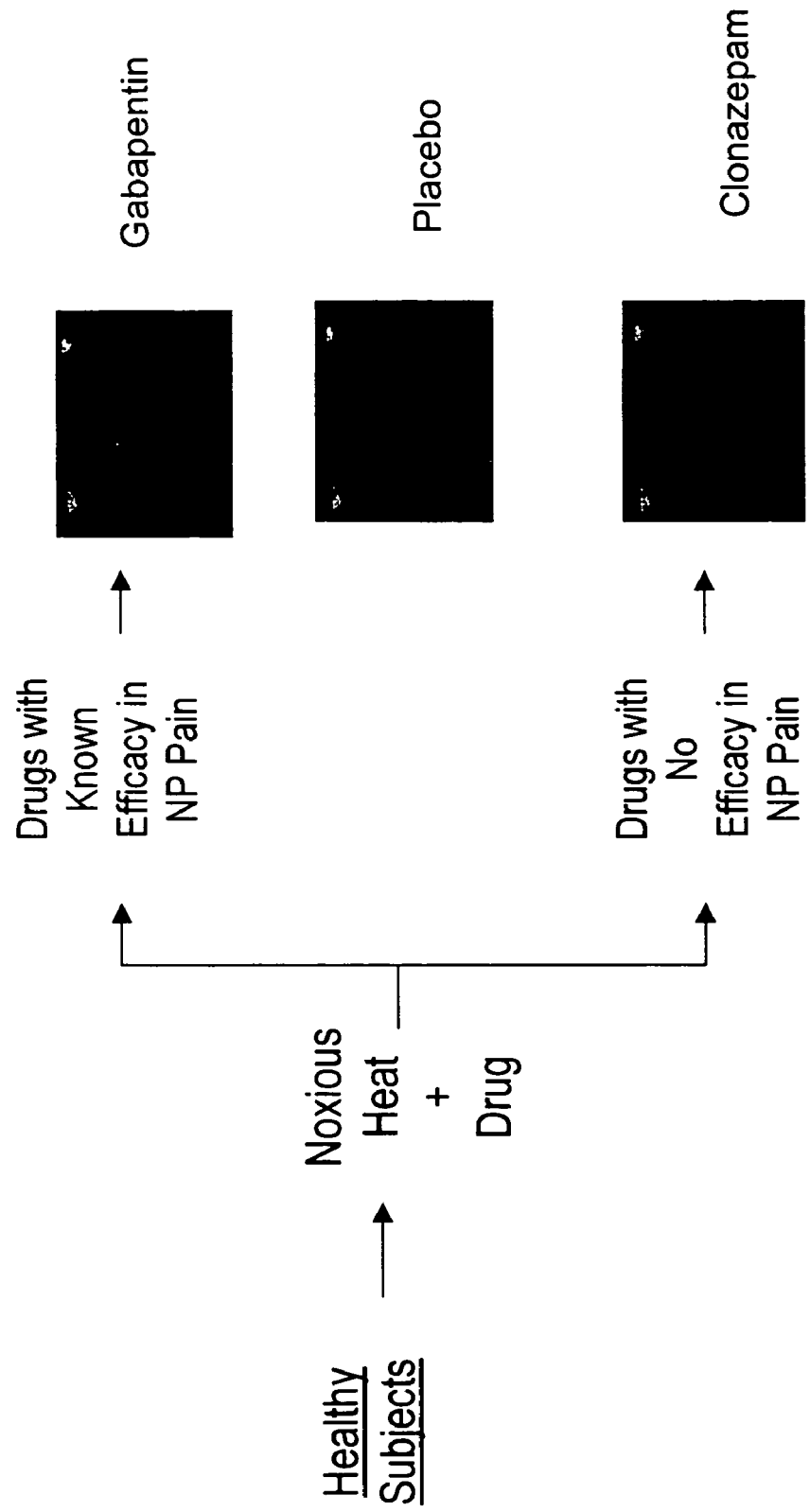
FIG. 5 is a series of fMRI images showing general CNS activation in rats following the use of a therapeutic compound with known efficacy (gabapentin) vs. one with no efficacy (clonazepam) in human neuropathic pain.
Figure 6:
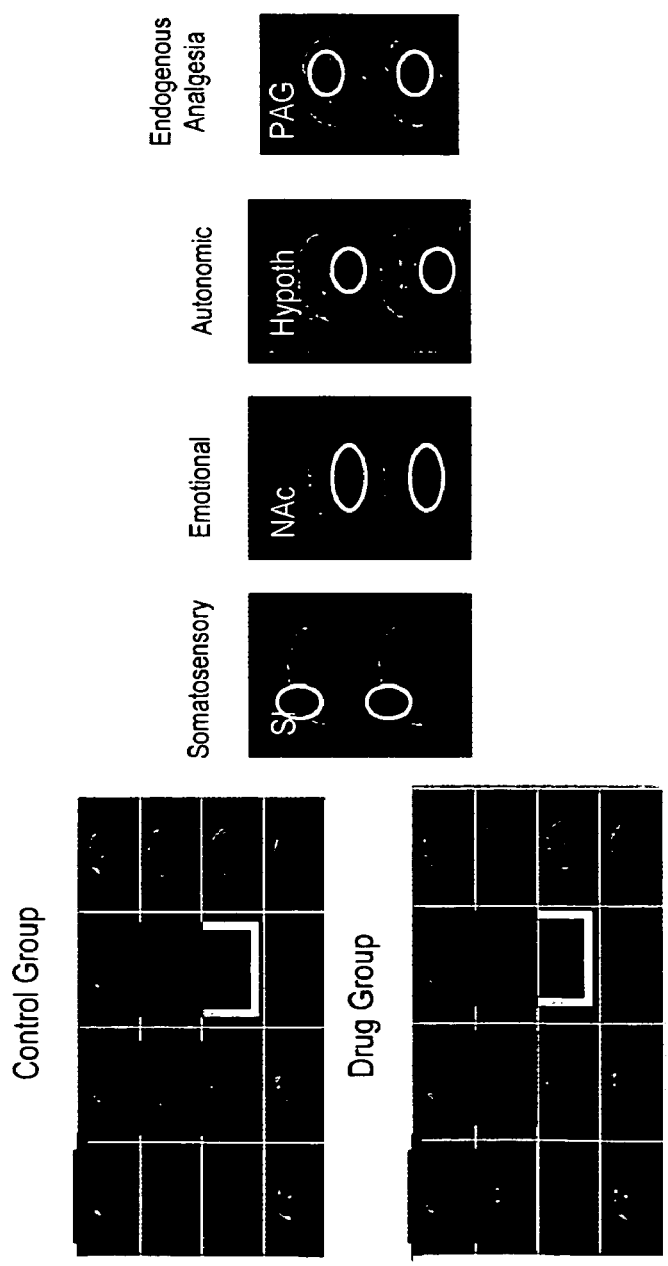
FIG. 6 is a series of fMRI images obtained in a rat model.

The methods of the invention may employ non-human mammals, e.g., rats, as the subjects, in which experimental therapeutic interventions are evaluated. FIG. 4 shows that the thermal response of rats was similar to that of humans for specific regions known to be involved in acute pain. These data provide evidence that rats may be used as a surrogate for humans in the methods of the invention. FIG. 5 shows the general CNS activation in rats following the use of a therapeutic compound with known efficacy (gabapentin) for neuropathic pain versus a compound with no efficacy (clonazepam). FIG. 6 shows the differences in CNS activation in more detail for gabapentin versus placebo in rats following heat stimulus. The left panels show serial coronal slices through the brain. The overall level of activation was decreased in the gabapentin group compared to the placebo group. The right panels show differences in activation in specific circuitry known to be involved in pain processing that was affected in somatosensory regions (SI), emotional regions (nucleus accumbens—NAc), autonomic regions (hypothalamus), and endogenous analgesic regions (periaqueductal gray).

Figure 7:
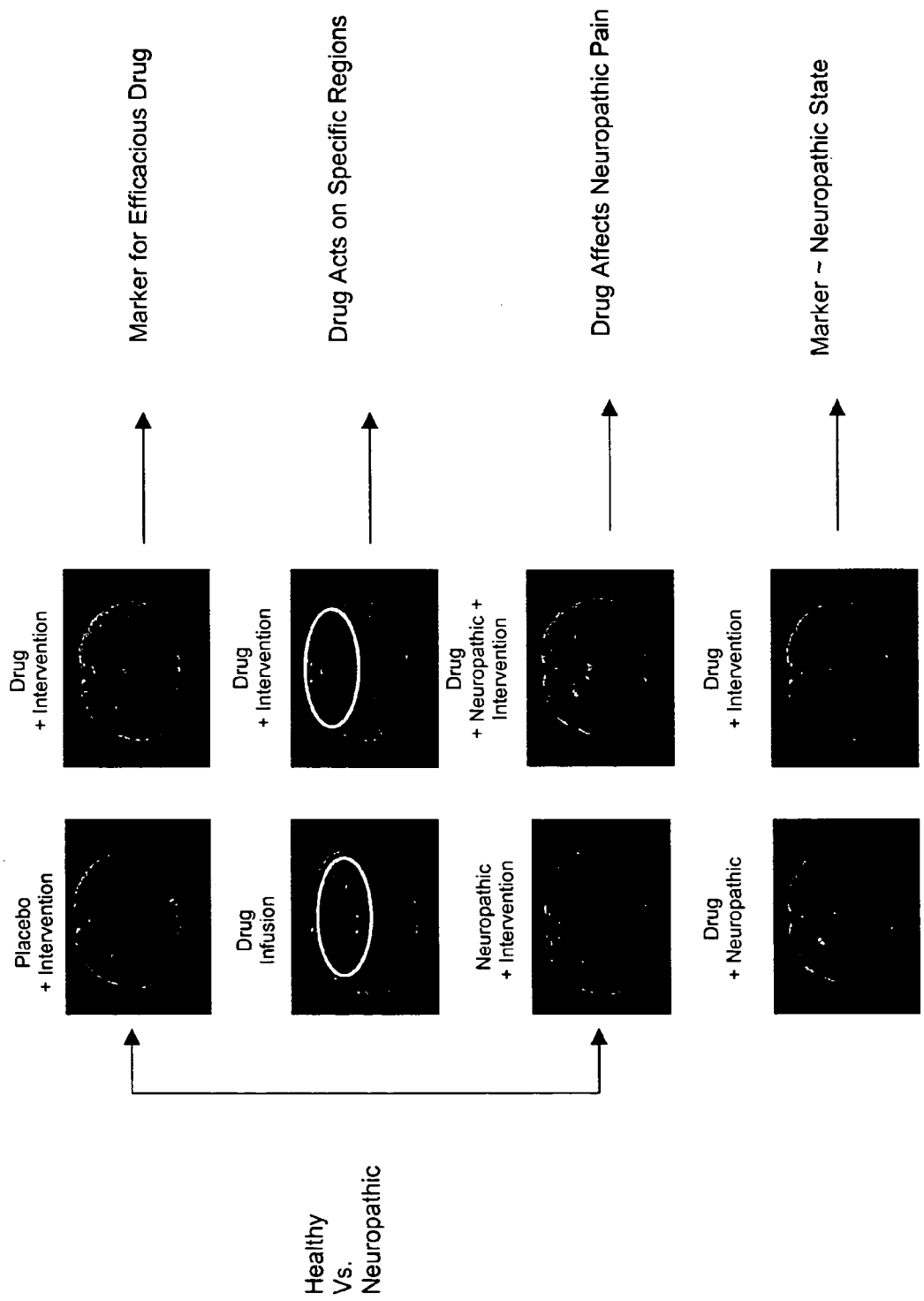
FIG. 7 is a series of fMRI images indicating the correlation of the heat stimulus with neuropathic pain.

FIG. 7 shows the correlation with the effect of the heat stimulus (i.e., an acute stimulus) versus neuropathic pain. The top two panels show how the therapeutic compound decreased activation after a heat stimulus compared to placebo—this is indicative of efficacy of a therapeutic intervention. The second row of panels shows the effects on the CNS of the therapeutic compound alone and the therapeutic compound after the heat stimulus—showing that the compound acts on specific regions. The third row of panels shows the effects of the heat stimulus on the CNS of a rat having neuropathic pain compared to CNS levels in a rat having neuropathic pain to which the therapeutic compound was administered. The results indicate that the compound affects the neuropathic condition. The last row of panels shows a comparison of the CNS levels after administration of the therapeutic compound to a rat having neuropathic pain and a rat to which the heat stimulus was administered, indicating that the acute painful stimulus applied to a healthy subject is a surrogate for drug efficacy on neuropathic pain.

EXAMPLE 3

Application to Psychiatric Disorders

Figure 8:
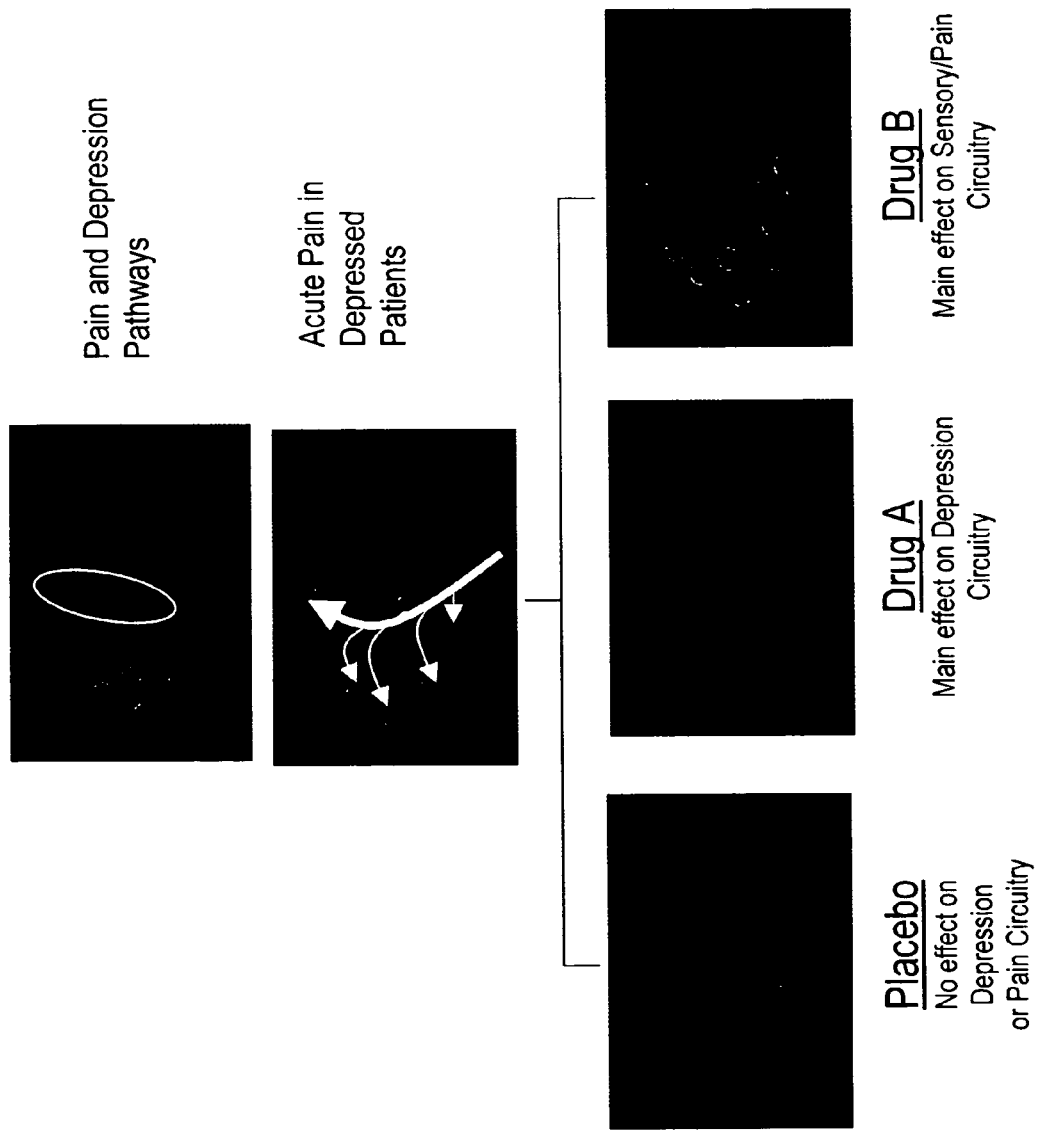
FIG. 8 is a schematic diagram for identifying therapeutic interventions for depression. A heat stimulus activates pathways that are common or overlap in pain and depression. The method may be used to evaluate drugs used for depression alone or for both pain and depression (e.g., antidepressants such as olanzepine, amitriptyline, and doxepin).

The methods of the invention may also be used to evaluate therapeutic interventions or develop markers for psychiatric disorders, e.g., depression. This approach is illustrated in FIG. 8. Pain and depression share some common circuitries. A notable exception is primary sensory systems (circled), which are not involved in depression. In one method, an acute pain stimulus may be used to activate regions of the brain that overlap in acute pain and depression to evaluate different classes of interventions that may have improved effects in depression alone or as analgesics. In another method, a stimulus that activates the circuitries involved in a psychiatric disorder, such as depression or anxiety, may be employed to evaluate therapeutic interventions for the disorder in healthy subjects or subjects suffering from the disorder. These methods are also broadly applicable to other psychiatric disorders, such as addiction and post traumatic stress disorder.

OTHER EMBODIMENTS

All publications, patents, and patent applications mentioned in this specification are hereby incorporated by reference to the same extent as if each independent publication or patent application was specifically and individually incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth, and follows in the scope of the appended claims.

Other embodiments are in the claims.

What is claimed is:

1. A method for identifying a therapeutic intervention for a functional illness, said method comprising the steps of:
   (a) administering a candidate therapeutic intervention to a subject;
   (b) administering an acute painful stimulus to said subject; and
   (c) measuring a level of activation of the central nervous system (CNS) indicative of said functional illness in said subject, wherein a modification of said level of CNS activation relative to a control level of activation characteristic of said functional illness is indicative of the efficacy of said candidate therapeutic intervention for said functional illness, wherein said level of activation is not measured with reference to specific regions of the CNS.

2. The method of claim 1, wherein said functional illness comprises neuropathic pain.

3. The method of claim 2, wherein said neuropathic pain comprises post herpetic neuralgia, HIV neuropathy, diabetic neuropathy, Fabry's disease, peripheral neuropathy, trigeminal neuralgia, post incisional neuropathic pain, phantom limb pain, reflex sympathetic dystrophy, causalgia, anesthesia dolorosa, intercoastal neuralgia, post-traumatic localized pain, complex regional pain syndrome, or neuropathic pain caused by trauma, lead, or chemotherapy.

4. The method of claim 1, wherein said acute painful stimulus comprises a change in temperature, mechanical force, a pin prick, or administration of a compound.

5. The method of claim 1, wherein said level of activation is measured by functional magnetic resonance imaging.

6. The method of claim 1, wherein said therapeutic intervention comprises a compound, a physical stimulus, an electrical stimulus, a thermal stimulus, electromagnetic radiation, counseling, or a surgical, medical, or dental procedure.

7. The method of claim 1, wherein said therapeutic intervention is administered subtherapeutically.

8. A method for identifying a therapeutic intervention for a psychiatric disorder, said method comprising the steps of:
  (a) administering a candidate therapeutic intervention to a subject;
  (b) administering an acute painful stimulus for said psychiatric disorder to said subject; and
  (c) measuring the level of CNS activation in said subject, wherein a modification of said level of CNS activation relative to a control level of CNS activation characteristic of said psychiatric disorder is indicative of the efficacy of said candidate therapeutic intervention for said psychiatric disorder, wherein said level of activation is not measured with reference to specific regions of the CNS.

9. The method of claim 8, wherein said psychiatric disorder comprises an affective disorder, an anxiety disorder, attention deficit hyperactivity disorder, a memory disorder, post traumatic stress disorder, a psychotic disorder, a substance abuse disorder, an addiction, a phobia, or obsessive compulsive disorder.

10. The method of claim 9, wherein said psychiatric disorder comprises depression, bipolar disorder, mania, dysphoria, anxiety, panic disorder, schizophrenia, or schizoaffective disorder.

11. The method of claim 8, wherein said level of activation is measured by functional magnetic resonance imaging.

12. The method of claim 8, wherein said therapeutic intervention comprises a compound, a physical stimulus, an electrical stimulus, a thermal stimulus, electromagnetic radiation, counseling, or a surgical, medical, or dental procedure.

13. The method of claim 8, wherein said therapeutic intervention is administered subtherapeutically.

* * * * *